(12) United States Patent
Jones et al.

(10) Patent No.: US 8,460,258 B2
(45) Date of Patent: Jun. 11, 2013

(54) METHODS AND APPARATUSES FOR THE TREATMENT OF WOUNDS WITH PRESSURES ALTERED FROM ATMOSPHERIC

(75) Inventors: Curtis E. Jones, Savannah, GA (US); John P. Kennedy, Pooler, GA (US)

(73) Assignee: Southeastern Medical Technologies, LLC, Savannah, GA (US)

( * ) Notice: Subject to any disclaimer, the term of this patent is extended or adjusted under 35 U.S.C. 154(b) by 209 days.

(21) Appl. No.: 12/811,155

(22) PCT Filed: Jan. 8, 2009

(86) PCT No.: PCT/US2009/000088
§ 371 (c)(1),
(2), (4) Date: Jun. 29, 2010

(87) PCT Pub. No.: WO2009/089016
PCT Pub. Date: Jul. 16, 2009

(65) Prior Publication Data
US 2010/0298791 A1     Nov. 25, 2010

Related U.S. Application Data

(60) Provisional application No. 61/010,410, filed on Jan. 8, 2008.

(51) Int. Cl.
*A61M 1/00* (2006.01)
(52) U.S. Cl.
USPC ........................................................ 604/319
(58) Field of Classification Search
None
See application file for complete search history.

(56) References Cited

U.S. PATENT DOCUMENTS

| | | | |
|---|---|---|---|
| 3,826,369 | A | 7/1974 | Murata et al. |
| 4,382,441 | A | 5/1983 | Svedman |
| 4,969,880 | A | 11/1990 | Zamierowski |
| 5,527,293 | A | 6/1996 | Zamierowski |
| 5,636,643 | A | 6/1997 | Argenta et al. |
| 5,645,081 | A | 7/1997 | Argenta et al. |
| 5,662,625 | A | 9/1997 | Westwood |
| 6,051,747 | A * | 4/2000 | Lindqvist et al. ............. 602/46 |
| 6,135,116 | A | 10/2000 | Vogel et al. |
| 6,553,998 | B2 | 4/2003 | Heaton et al. |
| 2003/0078532 | A1* | 4/2003 | Ruszczak et al. ............. 602/46 |
| 2004/0249353 | A1 | 12/2004 | Risks et al. |

(Continued)

FOREIGN PATENT DOCUMENTS

WO    WO 2008/027449    3/2008

OTHER PUBLICATIONS

Chariker, Mark E. et al., "Effective Management of Incisional and Cutaneous Fistulae with Closed Suction Wound Drainage", Contemporary Surgery, vol. 34, Jun. 1989, pp. 59-63.

(Continued)

*Primary Examiner* — Melanie Hand
*Assistant Examiner* — Andrew S Lo
(74) *Attorney, Agent, or Firm* — Nixon & Vanderhye P.C.

(57) ABSTRACT

The invention disclosed comprises methods, apparatuses and compositions to treat acute and chronic wounds with pressures altered from atmospheric. The methods, apparatuses and compositions herein improve the performance of altered pressure wound therapy. The improvements also make the treatments more comfortable for the patient and the delivery of the treatment more convenient for clinicians. These improvements collectively result in improved compliance, improved efficacy, improved safety and improved efficiency, while limiting clinical errors in treatment.

13 Claims, 8 Drawing Sheets

U.S. PATENT DOCUMENTS

| | | | |
|---|---|---|---|
| 2006/0264796 | A1 | 11/2006 | Flick et al. |
| 2007/0010778 | A1* | 1/2007 | Burrell et al. ............ 602/54 |
| 2007/0027414 | A1* | 2/2007 | Hoffman et al. ............ 602/2 |
| 2007/0055209 | A1* | 3/2007 | Patel et al. ............ 604/315 |
| 2007/0078366 | A1* | 4/2007 | Haggstrom et al. ............ 602/53 |
| 2007/0185426 | A1 | 8/2007 | Ambrosio et al. |
| 2007/0292488 | A1 | 12/2007 | Bassiri et al. |
| 2009/0306609 | A1* | 12/2009 | Blott et al. ............ 604/305 |

OTHER PUBLICATIONS

Davydov, Yu A. et al., "Vacuum Therapy in the Treatment of Purulent Lactation Mastitis", Vestnik Khirurgii Imeni Il-Grekova, vol. 137 (11), Nov. 1986, pp. 66-70.

Davydov, Yu. A. et al., "The Bacteriological and Cytological Assessment of Vacuum Therapy of Purulent Wounds", Vestnik Khirurgii, Oct. 1988, pp. 48-52.

Davydov, Yu A. et al., "Concepts for Clinical Biological Management of the Wound Process in the Treatment of Purulent Wounds Using Vacuum Therapy", Vestnik Khirurgii, Feb. 1991, pp. 132-135.

Kostiuchenok, B. M. et al., "The Vacuum Effect in the Surgical Treatment of Purulent Wounds", Vestnik Khirurgii, Sep. 1986, pp. 18-21.

Usupov, Y. N. et al., Active Wound Drainage, Vestnik Khirurgii, Apr. 1987, pp. 42-45.

* cited by examiner

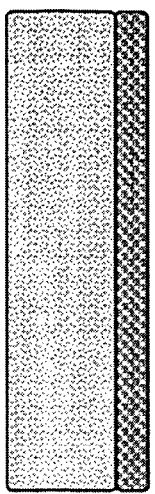
*Fig. 1-A*
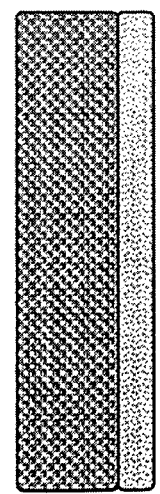
*Fig. 1-C*
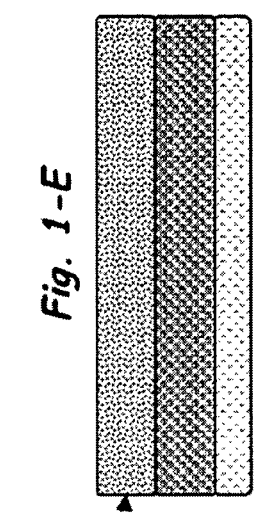
*Fig. 1-B*
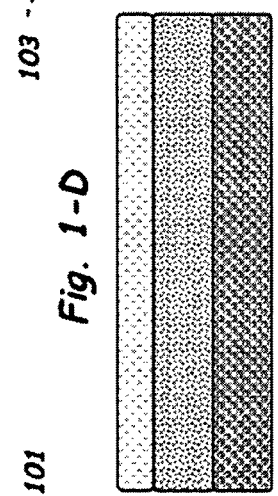
*Fig. 1-D*
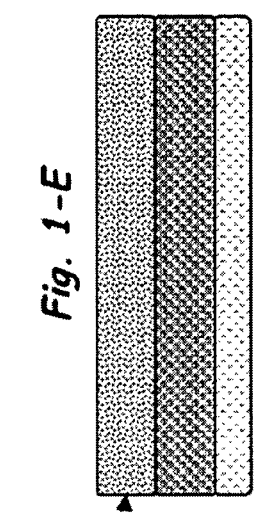
*Fig. 1-E*
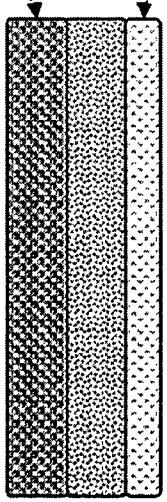
*Fig. 1-F*
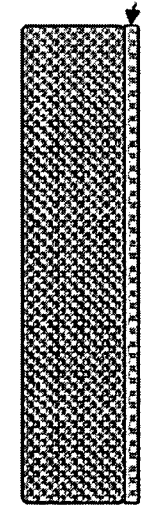
*Fig. 1-G*
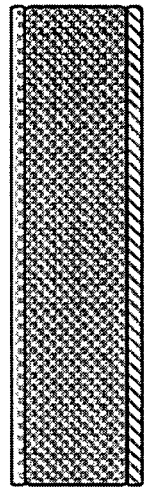
*Fig. 1-H*
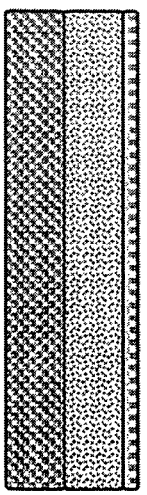
*Fig. 1-I*
Figure 1

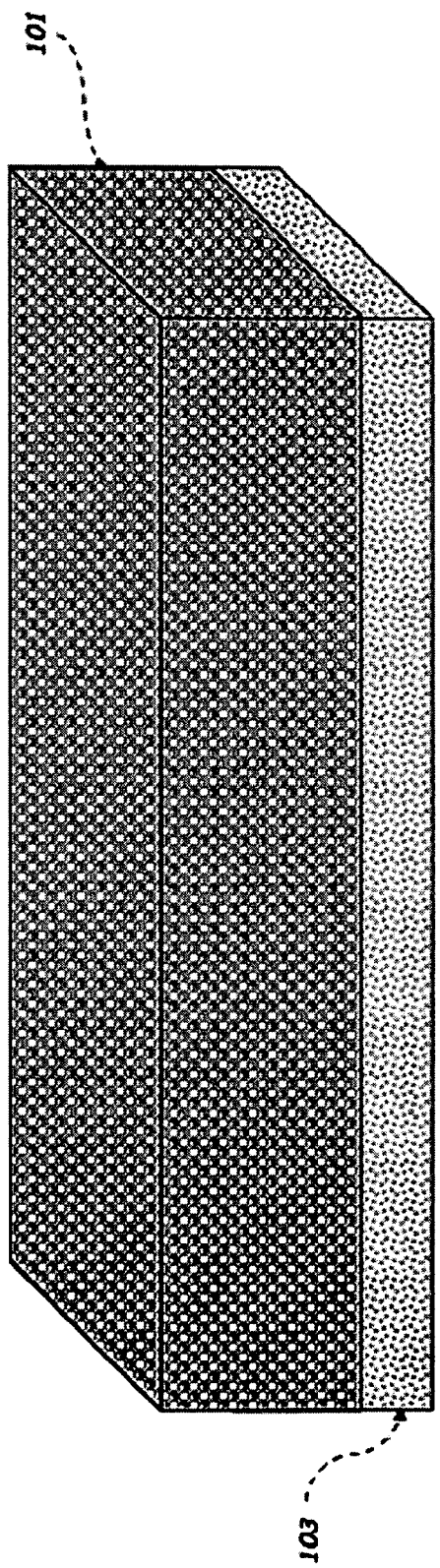
Fig. 2-A
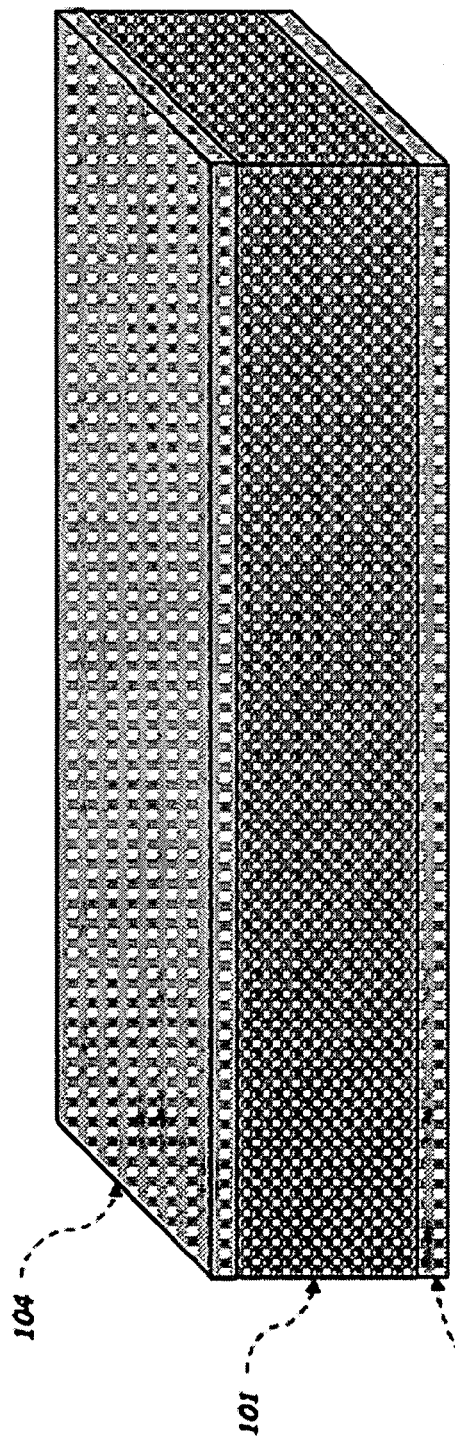
Fig. 2-B
Figure 2

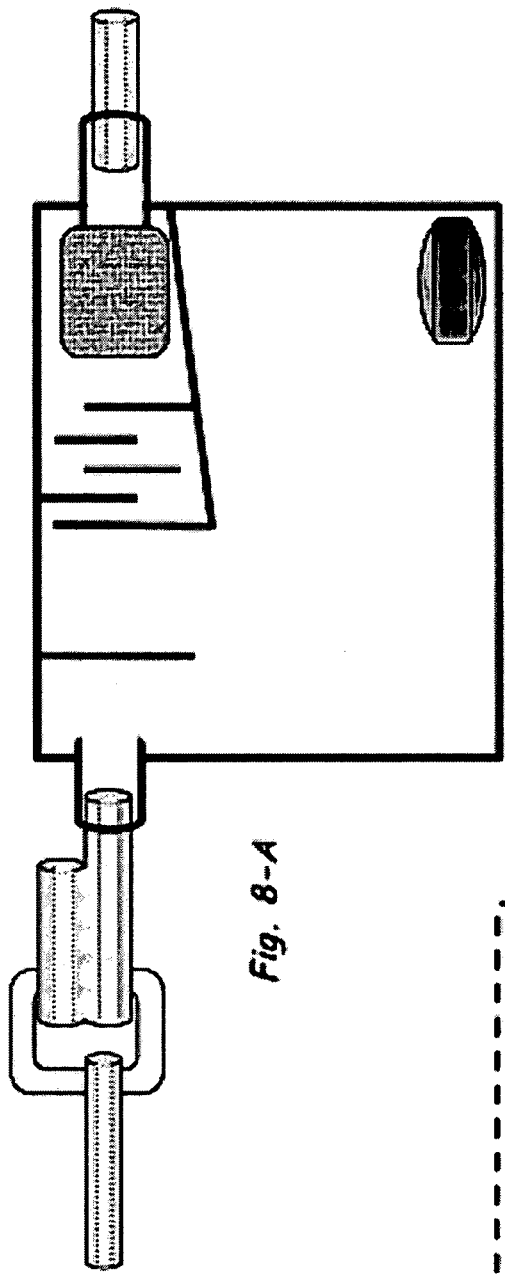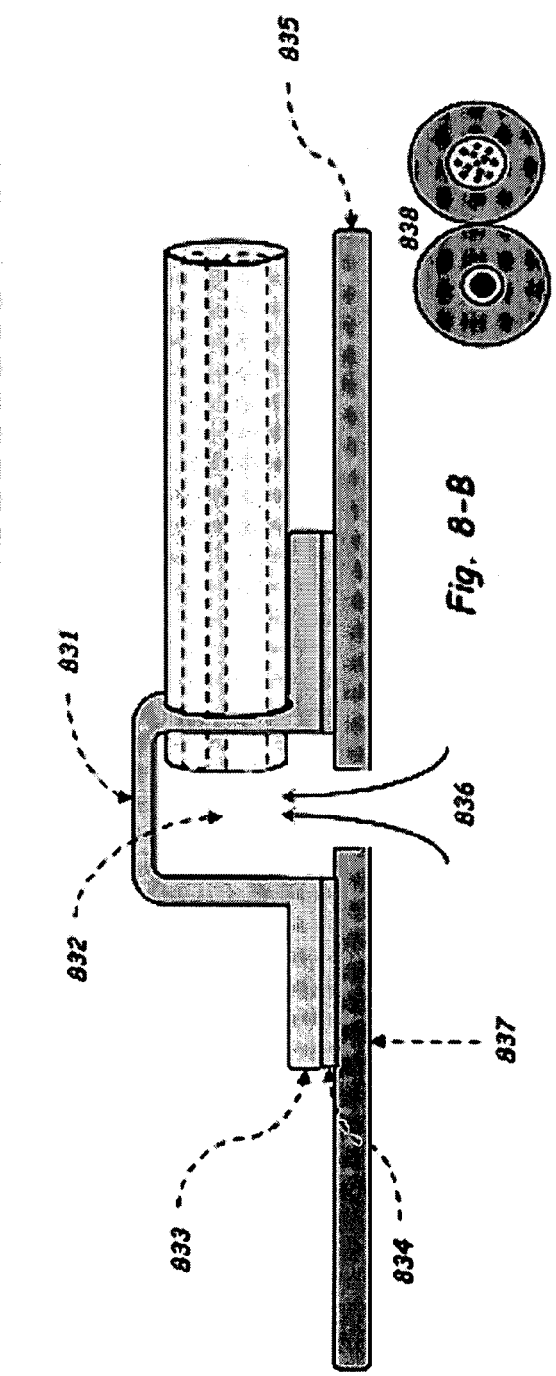

METHODS AND APPARATUSES FOR THE TREATMENT OF WOUNDS WITH PRESSURES ALTERED FROM ATMOSPHERIC

This application is the U.S. national phase of International Application No. PCT/US2009/000088 filed 8 Jan. 2009 which designated the U.S. and claims priority to U.S. Provisional Patent Application Ser. No. 61/010,410 filed 8 Jan. 2008, the entire contents of each of which are hereby incorporated by reference.

BACKGROUND OF THE INVENTION

1. Field of the Invention

This invention relates to generally to wound healing. In particular, the invention relates to wound healing with pressures altered both positively and negatively from atmospheric.

More specifically this invention is directed at apparatuses and methods that utilize layered intermediate material constructs, high gas-permeable cover constructs and pressure monitoring/control systems which are more convenient, safe and efficient for the clinician, more comfortable and less painful for the patient, and result in improved efficacy versus those of the prior art.

2. Background of the Invention

The need to rapidly close acute and chronic wounds has been a focus of research since the dawn of medical practice. The background art is characterized by therapeutic strategies utilizing pressures altered from atmospheric conditions. Such strategies have been practiced by clinicians for both acute and chronic wounds for over a hundred years. Positive pressure strategies began expanded utilization least by the early 1800's, while negative pressure wound therapy began institutional practice at least as far back as the early 1980's.

Positive pressure wound therapy began by employing large chambers that encapsulated the entire patient. While more locally focused pressures have been attempted, they proved problematic for the relatively high pressures utilized. Conversely, to date negative pressure wound therapy has been developed as a local site methodology, specific to a peripheral zone around the wound bed. Likewise, the present invention limits its application to the local tissue of and around the wound; however, it can utilize both negative pressures and positive pressures.

The following core features are common among the negative pressure wound therapy configurations known in the art, which employ a local site application methodology:
  a covering means adapted to protect a wound from contamination and/or trauma;
  a sealing means, optionally designed as a part of the covering means, for establishing intimate but reversible contact with the perimeter of said covering to surrounding skin surfaces of said wound, thereby creating an encapsulated space, including the wound bed under said covering;
  the sealing means further providing a seal competent enough to provide treatment of the wound with pressures purposefully altered to those lower than atmospheric;
  a pressure altering means for interfacing negative pressures from a source with the said encapsulated space to lower the pressure therein as desired, said pressure altering means working in combination with said covering and sealing means to maintain the so desired encapsulated space pressures;
  the pressure altering means comprising a proximal end, a medial section and a distal end;
  a negative pressure source for delivering the initial pressure differential to the pressure altering means; and optionally at least one of the following:
    a. the pressure altering means further consisting of a proximal end with direct physical access to the encapsulated space through an opening or conduit through said covering, and a distal end connected to the proximal end via a medial section, such distal end further adapted for connection to a negative pressure source; or
    b. the pressure altering means further consisting of a proximal end with direct physical access to the encapsulated space through a passage created between skin and sealing means of said covering, and a distal end connected to the proximal end via a medial section, such distal end further adapted for connection to a negative pressure source; or
    c. the pressure altering means further consisting of a proximal end with indirect access to the encapsulated space though a void or opening in said cover, and a distal end connected to the proximal end via a medial section, such distal end further adapted for connection to a negative pressure source; or
    d. the pressure altering means further consisting of a proximal end with indirect access to the encapsulated space through a passage created between skin and sealing means of said covering, and a distal end connected to the proximal end via a medial section, such distal end further adapted for connection to a negative pressure source.

The apparatus above generically encompasses the core features of the historical apparatuses in the literature and prior art.

3. Related Art

A search of the prior art did not disclose any patents that read directly on the claims of the instant invention; however, the following references were considered related.

Journal article "The vacuum effect in the surgical treatment of purulent wounds" by Kostiuchenok, II; Kolker, V A Karlov V A, et al.: *Vestnik Khirurgii* 1986 describes an intermittent manual application of minimal negative pressure to reduce bacterial counts and heal stubborn wounds.

Journal article "Vacuum therapy in the treatment of purulent lactation mastitis" by Davydov u A. Malafeeva, E. V., Smirnov A. P.: Vestnik Khirurgii Imeni I. I.—Grekova 1986 presents the retrospective results of over 100 patients presenting with purulent mastitis. The authors describe the techniques of intermittent application of various negative pressures and durations as used in their clinic since 1980, as well as efficacy results regarding these techniques.

Journal article "Active wound drainage" by Usupov, Y N; Yepifanov, M V: *Vestnik Khirugii* 1987 describes the authors methodology and results for determining apparent threshold and maximum negative pressures which attempt to project a therapeutic index for negative pressures from an animal model.

Journal article "The Bacteriological and cytological assessment of vacuum therapy of purulent wounds" by Davydov Yu A., Larichev A. B., Menkov, K. G.: Vestnik Khirurgii Imeni-i—Grekova 1988 describes the techniques for intermittent application of various negative pressures and durations and demonstrates the faster progression through healing stages of these patients compared to controls.

Journal article "Effective management of incisional and cutaneous fistulae with closed suction wound drainage" by Chariker, M E; Jeter, K F, et al.: *Contemporary Surgery* 1989 authors describe specific dressings and treatment methodologies including drains, screens, packings and covers which are readily available to world wide clinicians and readily adaptable to negative pressure therapy. The authors report on the training and efficacy of these methodologies for a specific hard to heal surgical wounds, namely fistulae complicated wounds.

Journal article "Concepts for clinical biological management of the wound process in the treatment of purulent wounds using vacuum therapy" by Davydov, Y A; Larichev, A B, Abramov A Y, et al.: *Vestnik Khirugii* 1991 authors report on expansion of applications of negative pressure techniques to various acute and chronic wounds as well as patient populations as expanded since their previous publication. Authors also describe attributes of negative pressure therapy that may explain its efficacy.

U.S. Pat. No. 4,382,441 issued in the name of Svedman; Pal teaches the composition of a wound dressing designed for irrigation treatment of a wound combined with suction. The dressing comprises (a) an impermeable cover, (b) at least two openings at opposing ends of the dressing and formed through the central section of the cover for subsequent insertion of both an irrigation tube and a suction tube, and (c) a porous intermediate material. No pressures are disclosed in this patent, but the implied intent is to keep the irrigation inlet, when operable, at atmospheric or very low positive pressure to avoid expansion and dislocation of the cover. Consequently the implied optimal suction outlet pressure, when operable, is slightly greater than the irrigation inlet pressure, thereby drawing and distributing the irrigant evenly through the porous intermediate material and evenly across the wound bed in a controlled delivery manner, without build up of the irrigant.

U.S. Pat. No. 4,969,880 issued in the name of Zamierowski; David S. teaches the composition of a wound dressing designed for negative pressure treatment of a wound that includes a semi-permeable cover with an adhesive sealing means, an opening formed through the central section of the cover for the introduction of a PAM, said PAM adapted for connection to a negative pressure source or a fluid source for introducing fluids. This patent also teaches a variety of intermediate materials which can be placed between the wound bed and the PAM under the cover. A method of wound treatment with the said dressing is also disclosed.

U.S. Pat. No. 5,527,293 issued in the name of Zamierowski; David S. teaches a specific method for fastening suction tubes (i.e. drains) to wound dressings designed for negative pressure wound therapy. Briefly, this fastening method for treating wounds with negative pressure comprises (a) applying a dressing to the wound; (b) adhering a polymer cover/seal to a foam material inserted between the cover and tissue; (c) applying negative pressure to the wound; and (d) directing fluid flow with the polymer cover/seal from wound surface through the foam material. The said dressing comprises preferably a semi-permeable adhesive polymer cover/seal.

U.S. Pat. No. 5,645,081 issued in the name of Argenta et al. teaches another method for wound treatment utilizing negative pressure, but utilizes an impermeable cover rather than semi-permeable, contrary to U.S. Pat. No. 4,969,880. The patent further teaches the use of intermediate materials in combination with impermeable covers with the PAM contained within or underneath the intermediate materials.

U.S. Pat. No. 5,636,643 issued in the name of Argenta et al. teaches another method for wound treatment utilizing negative pressure, but utilizes an impermeable cover rather than semi-permeable, contrary to U.S. Pat. No. 4,969,880. The patent further teaches the use of negative pressure adapted to specific wound types and specific durations of therapy.

U.S. Pat. No. 6,135,116 issued in the name of Vogel et al. teaches a method and apparatus for combining intermittent pneumatic compression and negative pressure wound therapy.

U.S. Pat. No. 6,553,998 issued in the name of Heaton et al. teaches negative pressure wound therapy that utilizes the combination of a suction head and a cover. More specifically, the suction head is designed with projections on the bottom flange, which prevent sealing or blockage of the suction head by providing flow channels for liquids to exit the wound via a PAM.

PCT/US2007/019033 filed in the name of Kennedy et al, the same inventors of this filing, teaches apparatuses and methods for treating wounds with altered pressures. Briefly, and relevant to the inventions and disclosures contained herein, the previous PCT filing discloses (a) PAM designs, especially relative to designs and components for terminal connections to altered pressure dressings; (b) anti-infective and anti-ingrowth compositions for use with altered pressure therapy; (c) specific canister designs; (d) intermediate material compositions; and (e) pressure sensing feedback designs.

Consequently, a need has been demonstrated for the invention which provides methods, apparatuses and compositions that: (a) improve the performance of altered pressure wound therapy (b) make the treatments more comfortable for the patient, and (c) make the administration of the treatment more convenient for clinicians. These improvements collectively result in improved efficacy, improved compliance, improved safety and improved performance, while limiting clinical errors in treatment.

SUMMARY OF THE INVENTION

The purpose of the invention is to provide apparatuses, or components thereof, devices and methods that improve the performance of altered pressure wound therapy, make the treatments more comfortable for the patient and the delivery of the treatment more convenient for the clinician. These combined benefits cascade to provide improved efficacy, improved patient compliance and improved performance, while limiting clinical errors in treatment.

A first aspect is an altered pressure apparatus and method for delivering altered pressure therapy to a wound. The apparatus and method comprises a layered intermediate material, either stacked or laminated, to optimize the interface between the intermediate materials adjacent contact surfaces (i.e. the interfaces of top, bottom and/or sides).

In broad terms, a preferred embodiment of the apparatus is comprised of independent material components including foams, woven textiles and/or nonwoven textiles of various attributes, including surface morphologies, chosen to provide specific advantages.

One advantage of the invention is that the layered components may be specified to improve patient comfort during altered pressure wound therapy, including less pain during dressing changes. Another advantage of the invention is that the layered components may be specified to optimize the tissue interface while independently maximizing the efficiency of exudate removal. Another advantage of the invention is that the layered intermediate materials may be sized simultaneously to improve clinician convenience by speeding the process of custom fitting the intermediate material to the morphology of the wound. Another advantage of the invention is that the layered components may be specified to improve the efficacy of altered pressure therapy by limiting trauma at the tissue interface and increasing compliance among patients. Another advantage of the invention is that the layered components may be specified to optimize the filtering efficiency and void filling when used in conjunction with semi-solid primary dressings.

Another aspect is an altered pressure apparatus and method for delivering altered pressure therapy to a wound. The apparatus and method comprises a high moisture vapor transmission rate covering means to maximizing the efficiency of exudate removal at negative altered pressures.

In broad terms, a preferred embodiment of the apparatus is comprised of a covering means with a moisture vapor transmission rate>1,000 $g/m^2/24$ hr measured at 37° C. and 10-90% relative humidity. A second preferred embodiment of the apparatus is comprised of a covering means with a moisture vapor transmission rate>5,000 $g/m^2/24$ hr measured at 37° C. and 10-90% relative humidity. A third preferred embodiment of the apparatus is comprised of a covering means with a moisture vapor transmission rate>10,000 $g/m^2/24$ hr measured at 37° C. and 10-90% relative humidity.

One advantage of the invention is greater exudate removal efficiency, including transport durations. Another advantage of the invention is the ability to use lower negative altered pressures, thereby causing less pain to the patients being treated. Another advantage of the invention is improving compliance by the patients. Another advantage of the invention is the high exudate removal efficiency combined with the lower pressures required complement the use of semi-solid primary dressings.

Another aspect is an altered pressure apparatus and method for delivering altered pressure therapy to a wound. The apparatus and method comprises a PAM with a means of monitoring the pressure of the encapsulated space by measuring the pressure between the wound and the canister outlet.

In broad terms, a preferred embodiment of the apparatus is comprised of a means for monitoring the pressure inside or outside of the encapsulated space within 10 cm from any PAM access opening in the cover, the apparatus further comprising a filter contained within the canister adapted to filter canister effluent. A second preferred embodiment of the apparatus is comprised of a means for monitoring the pressure located outside of the encapsulated space 10-120 cm from any PAM access opening in the cover, the apparatus further comprising a filter contained within the canister adapted to filter canister effluent. A third preferred embodiment of the apparatus is comprised of a means for monitoring the pressure located outside of the encapsulated space>120 cm from any PAM access opening in the cover up to the canister inlet, the apparatus further comprising a filter contained within the canister adapted to filter canister effluent. A fourth preferred embodiment of the apparatus is comprised of a means for monitoring the pressure located outside of the encapsulated space via the space within the canister, the apparatus further comprising a filter contained within the canister adapted to filter canister effluent.

One advantage of the invention is greater accuracy as compared to measuring pressures between the canister and pressure source. Another advantage of the invention is the ability to use lower profile tubing and connectors, thereby causing less pain and resulting in improved compliance by patients. Another advantage of the invention is the ability to use lower profile tubing and connectors, thereby causing less secondary trauma and secondary wounding. Another advantage of the invention is prevention of liquids, odors and bacteria from contaminating the pressure source and containment of potential hazards. Another advantage of the invention is limiting contact with the filter and filter components thereby providing greater convenience and less cross contamination by disposing of the filter and canister as a substantially contained unit.

Another aspect is an altered pressure apparatus and method for delivering altered pressure therapy to a wound. The apparatus and method comprises an anti-infective.

In broad terms, in a preferred embodiment the anti-infective is a semisolid. In another preferred embodiment the semisolid is a lipid. In another preferred embodiment the lipid is a fatty acid. In another preferred embodiment the lipid is a fatty acid ester.

One advantage of the invention is anti-infectives augment the ability of altered pressure wound therapy to control bacteria and biofilm formation. Semisolids, most preferably hydrophobic, also provide the advantages of limited trauma upon dressing changes, limited migration during pressure therapy, anti-granulation infiltration, malleable void fillers and prevention of over drying the wound. Advantages of lipids include anti-infective utility, reduced pain upon dressing changes, low cost, low resistance, low sensitization, low toxicity and good to biocompatibility.

Another aspect is an altered pressure apparatus and method for treating wounds. The apparatus and method comprises the utilization of an anti-granulation in-growth adhesion material.

In broad terms, in a preferred embodiment the anti-granulation material is an irritant. In another preferred embodiment the anti-granulation material is a lipid.

One advantage of the invention is that the anti-granulation material will limit in-growth within dressings and therefore greatly reducing trauma and pain upon dressing change.

Embodiments of the invention also provide that any of the disclosed apparatus components, semi-solids or intermediate materials may further comprise a therapeutic, including the following: a hemostasis or coagulation promoting agent; a vasoactive agent; a tissue growth stimulant or a healing promoter; an anti-infective agent; an anti-adhesive agent; a viscosity enhancer; an anesthetic; a solvent or co-solvent; an anti-inflammatory agent; a controlled-release component or composition; or any combination thereof.

Further aspects will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE DRAWINGS

The features of the invention will be better understood by reference to the accompanying drawings, which illustrate presently preferred embodiments of the invention.

FIG. 1 shows a side view of a minimum two component layered intermediate material. The intermediate material examples are shown with foam and textile matrix components. FIG. 1-A: Bi-layered foam (least porous size bottom), FIG. 1-B: Bi-layered foam (least porous top), FIG. 1-C: Tri-layered foam (porosity increases from bottom to top), FIG. 1-D: Tri-layered foam (porosity decreases from bottom to top), FIG. 1-E: Tri-layered foam (porosity: lowest bottom, highest core), FIG. 1-F: Bi-layered (foam top+woven bottom), FIG. 1-G: Bi-layered (foam bottom+nonwoven top), FIG. 1-H: Tri-layered (woven top & nonwoven bottom/foam core), FIG. 1-I: Tri-layered (woven bottom/foam core & top)

(top shown with highest porosity). FIG. 1 Notes: (a) "Least porous" is intended to indicate smaller pore size and higher pore count per linear inch. (b) Foam layers may be synthetic (e.g. polyurethane, PVA, etc.), biologic (e.g. proteinaceous) or natural (e.g. sponges), open cell, closed cell, hydrophilic or hydrophobic.

FIG. 2 shows a three dimensional view of minimum two component layered intermediate materials. The intermediate material examples are shown with foam and textile components. FIG. 2-A: Bi-layered foam (least porous size bottom), FIG. 2-B: Tri-layered (woven top & bottom/foam core).

FIG. 3-A: Bi-layered foam (least porous size bottom), FIG. 3-B: Bi-layered foam (least porous top), FIG. 3-C: Tri-layered foam (porosity increases from bottom to top), FIG. 3-D: Tri-layered foam (porosity decreases from bottom to top), FIG. 3-E: Tri-layered foam (porosity: lowest bottom, highest core), FIG. 3-F: Bi-layered (foam top+woven bottom), FIG. 3-G: Bi-layered (foam bottom+nonwoven top), FIG. 3-H: Tri-layered (woven top & nonwoven bottom/foam core), FIG. 3-I: Tri-layered (woven bottom/foam core & top), (top shown with highest porosity), FIG. 3-J: Bi-layered (foam bottom+nonwoven top). FIG. 3 Notes: (a) "Least porous" is intended to indicate smaller pore size and higher pore count per linear inch. (b) Foam layers may be synthetic (e.g. polyurethane, PVA, etc.), biologic (e.g. proteinaceous) or natural (e.g. sponges), open cell, closed cell, hydrophilic or hydrophobic, (c) hydrophobic semi-solids include those of liquid crystal forming substances, (d) semi-solid is shown on the bottom in most figures for simplicity, but semisolid may be disposed on all tissue contact surfaces as shown in 3-J to maximize benefits.

FIG. 4-A: Tri-layered (woven top & bottom/foam core).

FIG. 5-A: Single central zone of adhesive void, FIG. 5-B: Multiple central zone of adhesive voids, FIG. 5-C: Universal patterned multiple zone of adhesive voids, FIG. 5-D: Universal patterned multiple zone of adhesive voids.

FIG. 6-A: Removable top canister illustration of multi-lumen feedback control system, FIG. 6-B: Illustration of alternate partially capsulated union designs, FIG. 6-C: Illustration of alternate tubing designs for the multi-lumen feedback system.

FIG. 7-A: Fixed top canister illustration (side view) of multi-lumen feedback control system. Canister further comprising a partial enclosure and baffle partitions to protect filter, FIG. 7-B: Fixed top canister illustration (top down view) of multi-lumen feedback control system (partial enclosure, inlet/outlet and baffle partitions shown in an alternate configuration).

FIG. 8 shows a partially dissected view of a multi-lumen feedback & filtering system. The system is illustrated with a second fixed top canister design. FIG. 8-A: Fixed top canister illustration of multi-lumen feedback control system (partial enclosure, inlet/outlet and baffle partitions shown in an alternate configuration), FIG. 8-B: Illustration of multi-lumen feedback system where the feedback is provided from the terminated proximal end of the tubing portion of the PAM.

Figure 3:
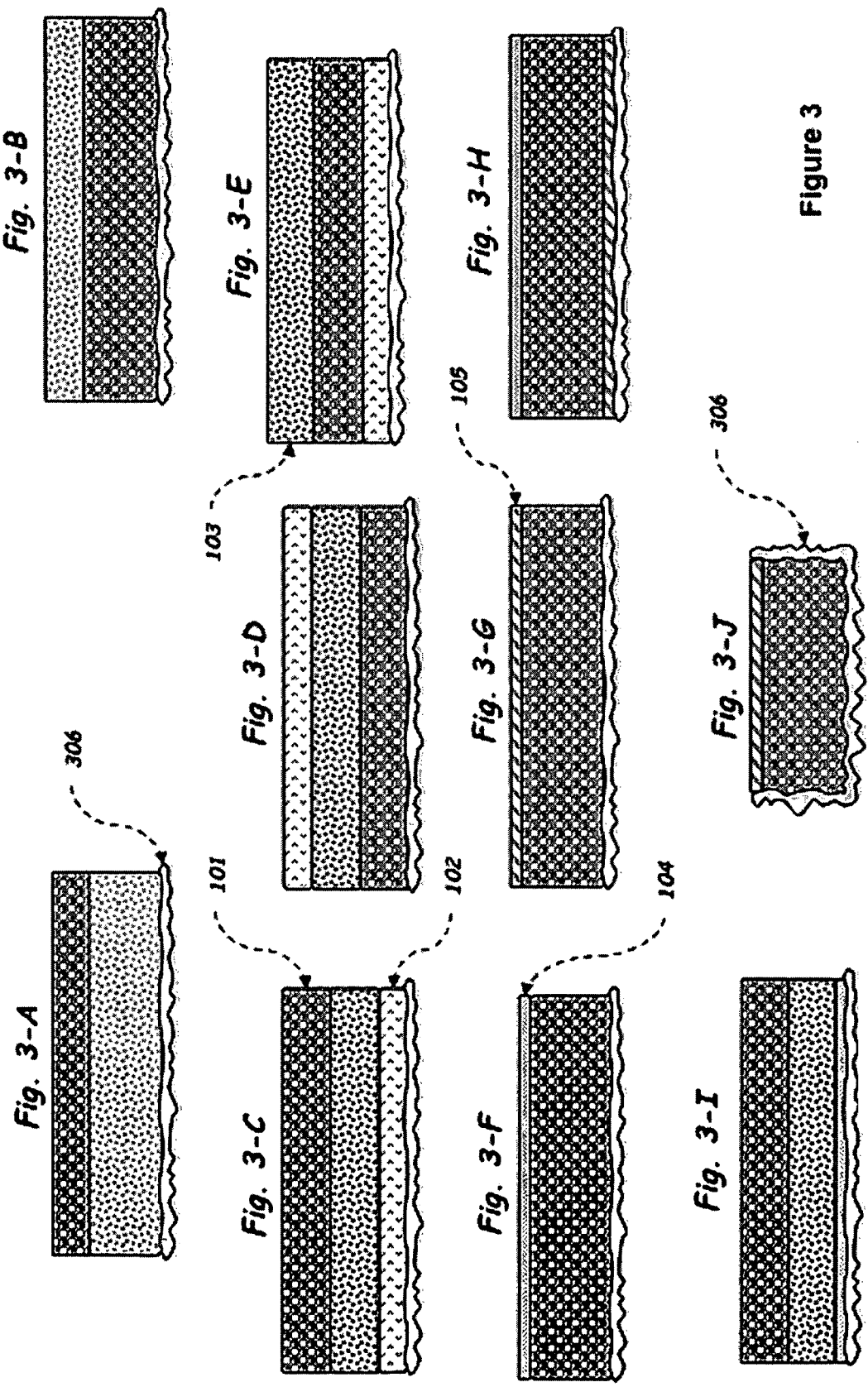
FIG. 3 shows a dissected view of a minimum two component layered intermediate material. The intermediate material examples are shown with a semi-solid primary material used in combination.

Figure Label Descriptions: 101—depicts the foam of greatest relative porosity, 102—depicts the foam of least relative porosity, 103—depicts the foam of median relative porosity, 104—depicts a woven material layer and 105—depicts a nonwoven material layer, 306—depicts a semi-solid primary material between the layered intermediate and the wound tissue, 407—depicts a few random areas where the semi-solid is optionally not continuous, or zones of semisolid void as typical of manual application, 508—depicts zones of adhesive voids in various shapes, which are not critical, 509—depicts areas of substantially continuous adhesive, 610—depicts a partially capsulated union of the tubing originating at the dressing (single lumen shown) and the multiple lumen (dual shown) which comprises a pressure sensing lumen (613), 611—depicts a multi-lumen tubing (dual lumen shown), 612—depicts a lumen for connection to and fluid communication with the encapsulated space, said tube is preferably a single lumen configuration for the illustrated example, 613—depicts a pressure sensing lumen, 614—depicts a pressure delivering lumen, 615—depicts the canister inlet, 616—depicts the canister outlet, 617—depicts the tubing communicating with the pressure source, 618—depicts the internal mouth of the inlet, 619—depicts a filter, as described herein, positioned to filter the outlet effluent, 620—depicts the bulk cavity of the canister, 621—depicts an optional fluid gelling means and/or a chlorinated additive, 622—depicts the removable top to the canister (threaded as shown), 623—depicts single tube, dual lumen examples, 624—depicts a dual passage coaxial example, 625—depicts dual tube, flattened (i.e. low profile) examples, 626—depicts other dual lumen, low profile examples [Note: Where dual lumen tubing is shown, alternate multi-lumen designs exist that contain greater than two lumen.], 727—depicts an opening to the partial enclosure containing the filter, 728—depicts a wall to the partial enclosure containing the filter, 729—depicts baffle partitions, 730—depicts a partial wall of separation between the inlet and filter, 831—depicts a connector portion of the PAM adapted to attach the terminated proximal end of the tubing portion of the PAM to the wound dressing, 832—depicts a supra space, created by the connector portion of the PAM, above the encapsulated space in communication with the pressure sensing lumen (613), 833—depicts the flat flange of a connector portion of the PAM mounted on top of the cover via an adhesive washer (834), 834—depicts a double adhesive washer, alternately to direct adhesive, for fixation of the connector over the opening to the encapsulated space, 835—depicts the cover, preferably semi-permeable as known in the art, 836—depicts an opening in the cover and the directional flow of wound fluids under negative altered pressures (for example), 837—depicts the wound faces side of the cover for orientation purposes, and 838—depicts alternative designs for the connector from a bottom up view.

DESCRIPTION OF SPECIFIC EMBODIMENTS OF THE INVENTION

Definitions

As used in this description and the accompanying claims, the following terms shall have the meanings indicated, unless the context otherwise requires:

"Nonwoven" as broadly defined and used herein, means fabric or cloth comprising an assembly of textile fibers (oriented in one direction or in a random manner) held together (1) by mechanical interlocking; (2) by fusing of thermoplastic fibers or (3) by bonding with a rubber, starch, glue, casein, latex or a cellulose derivative or synthetic resin. nonwoven textiles are neither woven, knitted, crocheted or knotted in order to maintain their structure but they can be fused into an ordered mesh.

"Woven" as broadly defined and used herein, means fabric or cloth formed by weaving, knitting, crocheting or knotting. More generally a woven fabric is made or constructed by interlacing threads or strips of material or other elements into a whole i.e. "woven fabrics". Many natural fiber "tissue textiles" are produced as woven articles.

"Layered" as broadly defined herein and used to reference intermediate materials shall mean any intermediate material constructed by two or more layers (or "stratums") of component materials. The said layered component materials may be either stacked or laminated.

"Laminate" as broadly defined and used herein, means a material constructed by uniting two or more layers (or "plies") of component materials together with very limited intermingling at the interface. As used herein, the process of creating a laminate is lamination, which requires creating a laminate by bonding the layers, including by means of heat, solvent, pressure and/or an adhesive.

"Liquid Crystal" as broadly defined and used herein, means any substance that exhibits a phase of matter that has properties between those of a conventional liquid, and those of a solid crystal. By example, a liquid crystal may flow like a liquid, but have the molecules in the liquid arranged and oriented in a crystal-like way. The phases can be distinguished and verified by optical properties and other methods. Examples of liquid crystal forming substances include amphiphilic molecules.

"Therapeutic" when used herein means having or exhibiting the ability to heal, treat or provide other benefits, including a substance or composition having or exhibiting the ability to heal, treat or generally provide a benefit. As used herein, therapeutic agents encompass augmentative agents, having or exhibiting the ability to enhance or provide a desired physical attribute or attributes of a system thereby impacting the performance of the system for the intended use. Examples of augmentative agents are viscosity enhancers and swelling agents. "therapeutic" when used herein as an adjective, means broadly having or exhibiting the ability to heal, treat or provide other benefits. Therapeutic when used herein as an adjective includes augmentative. When used as a noun herein, therapeutic or therapeutic agent, shall mean a substance or composition having or exhibiting the ability to heal, treat or provide other benefits. When used herein as a noun, a therapeutic or therapeutic agent shall include an augmentative agent. Examples of therapeutics are astringents and irritants.

"Augmentative" when used herein as an adjective, means broadly having or exhibiting the ability to enhance or provide a desired physical attribute or attributes of a system which impacts the performance of the system for the intended use. Therefore, an "augmentative agent" when used herein means a substance or composition having or exhibiting the ability enhance or provide at least one desired physical attribute which impact the performance of the composition for the intended use. Examples of augmentative agents are viscosity enhancers and absorbing agents.

"Anti-infective" when used as an adjective or adverb herein, means broadly having or exhibiting the ability to limit, arrest or reduce the growth, attachment, colonization or quantity of infective micro organisms, including planktonic or biofilm phenotypes such as pathogenic and nonpathogentic bacteria, viruses, fungi, and yeasts. When used as a noun herein, or as a noun derivative, the noun means any substance or composition having or exhibiting the ability to limit, arrest or reduce the growth, attachment, colonization or quantity of infective micro organisms, including planktonic or biofilm phenotypes such as pathogenic and nonpathogentic bacteria, viruses, fungi, and yeasts.

"Primary Material" when used herein shall mean any foreign material, any collection of foreign materials, or any composition of foreign materials inserted or incorporated into an encapsulated space of a wound bed that separates and prevents the direct contact of other foreign objects with the wound bed. Examples include a primary dressing separating the tissue bed from a specified foreign object.

"Secondary Material" when used herein shall mean any foreign material, collection of foreign materials or any composition of foreign materials inserted or incorporated into an encapsulated space of a wound bed that contacts at least a portion of an intermediate material. Examples include extra wound packing materials to eliminate adjoining dead space.

"Intermediate Material" when used herein shall mean any material inserted or incorporated into an encapsulated space of a wound bed that separates and prevents the direct contact of foreign objects with the wound bed or other foreign objects. Examples include: primary materials separating foreign objects from the tissue bed, any foreign materials separating two other objects, any collection of foreign materials separating objects and any composition of foreign materials separating objects.

"Encapsulated Space" when used herein shall mean the space bounded by the covering, sealing means and tissues with a perimeter of the sealing means. For the purposes herein, an imaginary line may be drawn on any breach of the space, in alignment with the midline of the covering or threshold of the peripheral sealing means, to generally indicate the descriptive boundary for the encapsulated space.

"Top" when used herein in reference to orientation around a wound shall mean the side or position farthest from the patient's wound bed. For clarification a "top" side would not contact the wound bed.

"Bottom" when used herein in reference to orientation around a wound shall mean the side or position closest to the patient's wound bed. For clarification a "bottom" side could contact the wound bed provided an intermediate material (or primary) is not present.

When referring to a PAM, "Proximal" as used herein with the exception of Venturi designs, shall generally mean within ten inches of the end positioned at the wound, but short of any bulk collecting means (i.e. "canister). Venturi designs are configured typically with the collection means at the proximal-medial portion, but can be a continuous loop.

When referring to a PAM, "Distal" as used herein with the exception of Venturi designs, shall generally mean within ten inches of the end positioned at altered pressure source, but not including such source. Venturi designs are configured typically with the altered pressure source at the medial-distal portion, but can be a continuous loop.

When referring to a PAM, "Medial" as used herein with the exception of Venturi designs, shall generally mean the section of the PAM between the proximal and distal ends. Venturi designs are configured typically with the wound/encapsulated space at the medial section, but can be a continuous loop.

"Altered Pressure" when used herein shall mean any pressure differing atmospheric pressure at the geographical location of patient either positively or negatively.

"PAM" when used herein shall be an abbreviation for "pressure altering means" as referenced as a component of the altered pressure apparatus in these definitions.

"Lumen" when used herein shall mean an enclosed channel or passages. As used herein, lumen is expressly not limited to tubular structures as the term is most commonly used in anatomical text, but also includes inanimate structures of non-tubular shapes. Both lumens and lumina are acceptable plural versions.

"Hydrophobic" when used herein shall mean any substance or composition lacking an affinity for water. For the purpose of this filing, other than references to foam, any substance or component of a composition with an aqueous solubility less than 1 g solute per 1000 g of solvent, shall be considered hydrophobic. For the purpose of this filing, any lipophilic or hydrocarbon rich substance or composition shall also be considered hydrophobic. For the purpose of this filing, any composition of foam adapted to augment absorption into the polymer backbone shall be deemed hydrophilic (e.g. polyether polyurethane) and any composition of foam adapted to attenuate absorption into the polymer backbone shall be deemed hydrophobic (e.g. polyester polyurethane).

"Altered Pressure Apparatus" when used herein shall mean an apparatus for treating wounds with the following features in combination:
  a covering means adapted to protect a wound from contamination and/or trauma;
  a sealing means, optionally designed as a part of the covering means, for establishing intimate but reversible contact with the perimeter of said covering to surrounding surfaces of said wound including skin, thereby creating an encapsulated space including the wound bed under the covering;
  the sealing means further providing a seal competent enough to provide treatment of the wound with pressures purposefully altered from atmospheric;
  a pressure altering means for communicating Altered Pressures from a source with the said encapsulated space to alter the pressure therein as desired, said pressure altering means working in combination with said covering and sealing means to maintain the so desired encapsulated space pressures;
  the pressure altering means comprising a proximal end, a medial section and a distal end;
  an altered pressure source for delivering the initial pressure differential to the pressure altering means; and optionally at least one of the following:
    i. the pressure altering means further consisting of a proximal end with direct physical access to the encapsulated space through an opening or conduit through said covering, and a distal end connected to the proximal end via a medial section, the distal end further adapted for direct or indirect connection to an altered pressure source; or
    ii. the pressure altering means further consisting of a proximal end with direct physical access to the encapsulated space through a passage created between skin and sealing means of said covering, and a distal end connected to the proximal end via a medial section, such distal end further adapted for direct or indirect connection to an altered pressure source; or
    iii. the pressure altering means further consisting of a proximal end with indirect access to the encapsulated space though a void or opening in said cover, and a distal end connected to the proximal end via a medial section, such distal end further adapted for direct or indirect connection to an altered pressure source; or
    iv. the pressure altering means further consisting of a proximal end with indirect access to the encapsulated space through a passage created between skin and sealing means of said covering, and a distal end connected to the proximal end via a medial section, such distal end further adapted for direct or indirect connection to an altered pressure source.

The present invention includes apparatuses, devices and methods for the treatment of acute and chronic wounds. This invention is particularly useful for treatment of acute and chronic wound that require closure to limit the potential for negative clinical progressions such as continued debilitation, pain and the development clinical or worsening of infection. The materials utilized for the covering means may be classified as impermeable, semi-permeable, permeable, non-occlusive, occlusive, partially occlusive or combinations thereof provided there permeability does not jeopardize the ability to alter pressures of the encapsulated space. However, preferably, the materials utilized for the covering means will be "semi-permeable" and "non-occlusive" as known commonly in medical practice.

I. Layered Intermediate Materials

Broadly a preferred system is disclosed to optimize the interface between intermediate materials and adjacent contact surfaces (i.e. the interfaces between the top, bottom and/or sides of the construct).

The system comprises the utilization of layered intermediate materials with altered pressure wound therapy.

Referring to FIGS. 1 & 2, the best mode of the invention employs layered intermediates comprising woven, non-woven and/or foam materials specified based on the required utility at the relevant interface.

A second best mode of the invention employs layered intermediates comprising hydrophilic and/or hydrophobic materials specified based on the required utility at the relevant interface.

A third best mode of the invention employs layered intermediates comprising natural, synthetic and/or biological materials specified based on the required utility at the relevant interface.

A fourth best mode of the invention employs layered intermediates comprising proteinaceous materials specified based on the required utility at the relevant interface.

Figure 4:
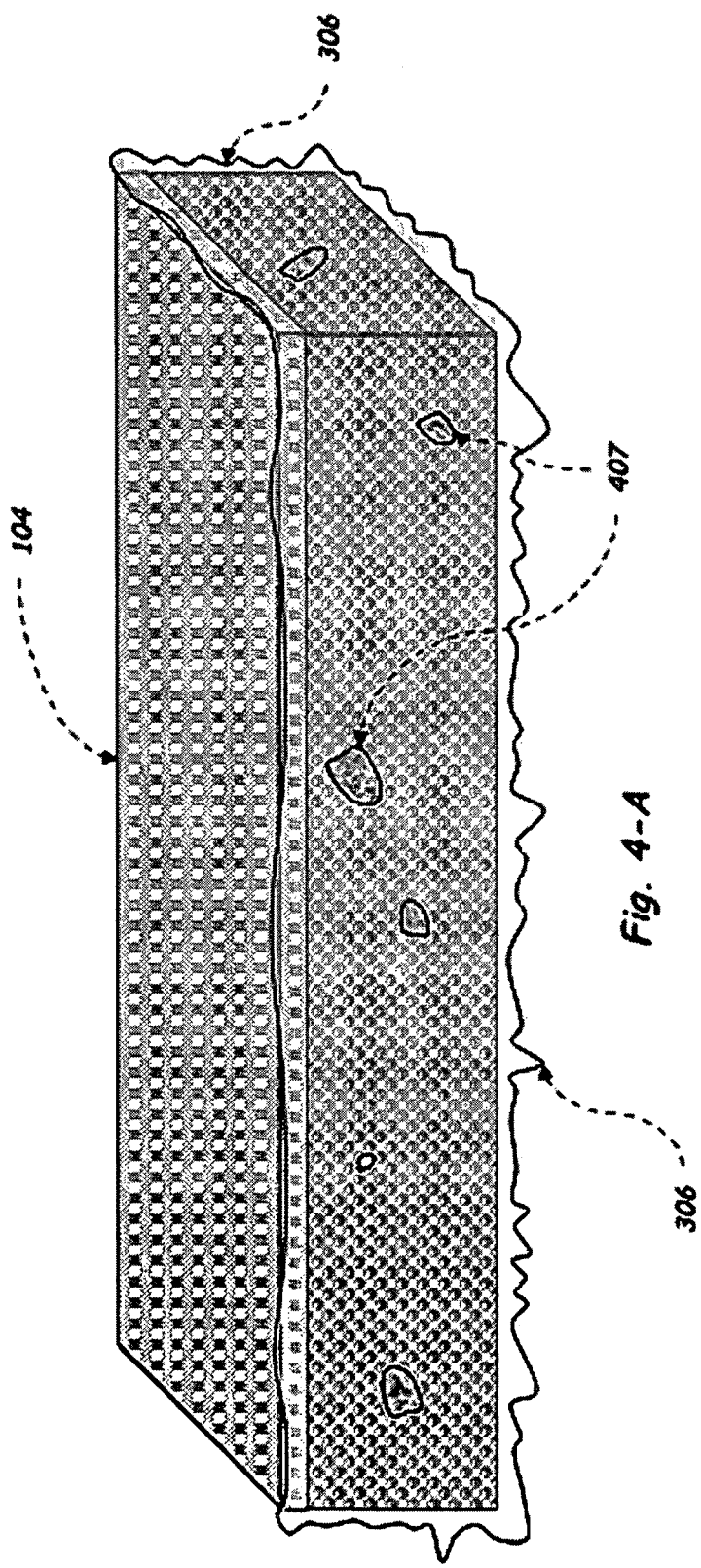
FIG. 4 shows a three dimensional view of a minimum two component layered intermediate material. The intermediate material example is shown with a semi-solid primary material used in combination.

Referring to FIGS. 3 & 4, a fifth best mode of the invention employs layered intermediates used in combination with the semi-solids disclosed herein as a primary material.

One method of the invention may be operated by applying a stacked or laminated layered intermediate material into the wound bed; enclosing the wound and said intermediate material into an encapsulated space by substantially sealing the space with a covering means adapted to include a sealing means; providing an opening in the covering means for a PAM to access or otherwise communicate with the Encapsulated space; and attaching the PAM to a canister in communication with an altered pressure source. Another method of the invention may be operated by applying a stacked or laminated layered intermediate material into the wound bed with a semi-solid as disclosed herein disposed substantially at the tissue interface; enclosing the wound and said intermediate materials into an encapsulated space by substantially sealing the space with a covering means adapted to include a sealing means; providing an opening in the covering means for a PAM to access or otherwise communicate with the Encapsulated space; and attaching the PAM to a canister in communication with an altered pressure source. Another method of the invention may be operated by applying a lipid based liquid crystal semi-solid between the tissue and the layered intermediate material to provide patient benefits including greater comfort during therapy, greater comfort during dressing changes, and limitation of microbial growth within the wound. Another method of the invention may be operated by applying a lipid based liquid crystal semi-solid to the wound bed; then applying the layered intermediate material. Another method of the invention may be operated by at least partially coating the layered intermediate material with a lipid based liquid crystal semi-solid prior to application of the layered intermediate material to the wound bed.

The embodiments are further described by the following aspects:

1. An altered pressure apparatus comprising layered intermediate materials.
2. The layered intermediate materials of item 1 where at least one layer is stacked.
3. The layered intermediate materials of item 1 where at least one layer is laminated.
4. The layered intermediate materials of item 2 where each layer is adapted to possess substantially the same footprint as the adjacent layer.
5. The layered intermediate materials of items 2-4 comprising at least one layer of woven, nonwoven or foam material.
6. The layered intermediate materials of item 5 comprising at least one layer of hydrophilic or hydrophobic material.
7. The layered intermediate materials of item 5 comprising at least one layer of natural, synthetic or biological material.
8. The layered intermediate materials of item 5 comprising at least one layer of proteinaceous material, including lactoferrin, collagen or gelatin based materials.
9. The layered intermediate materials of item 5 where the tissue contact layer is adapted to be at least partially an anti-granulation in-growth layer.
10. The altered pressure apparatus of item 5-9 further comprising a semi-solid material disposed between at least a portion of the intermediate materials and the wound tissue.
11. The semi-solid of item 10 adapted to be hydrophobic.
12. The semi-solid of item 10 further comprising a liquid crystal forming compound.
13. The semi-solid of item 10-11 at least partially composed of a lipid.
14. The semi-solid of item 12 at least partially composed of a lipid.
15. The semi-solid of item 14 at least partially composed of a fatty acid ester.
16. The semi-solid of item 15 where the fatty acid ester is selected from the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monocthiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate, polyoxyethylene (20) sorbitan monolaurate, polyoxyethylene (20) sorbitan monopalmitate, polyoxyethylene (20) sorbitan monostearate, polyoxyethylene (20) sorbitan monooleate, or combinations thereof and preferably glycerol monooleate or glycerol monoerucate if cost effective, highly viscous liquid crystalline states are desired.
17. The semi-solid of items 10-16 at least partially composed of a fatty acid including caprylic acid, capric acid, lauric acid, myristic acid, myristoleic acid, palmitic acid, palmitoleic acid, oleic acid, or combinations thereof.
18. The semi-solid of items 10-17 adapted to be at least partially an anti-infective composition.
19. The semi-solid of items 10-18 adapted to be at least partially an anti-granulation in-growth composition.
20. The altered pressure apparatus of item 1-19 where the negative altered pressures for treatment are less than 105 mm Hg.

II. Intermediate Materials for Use in Layers

Broadly preferred intermediate material configurations are disclosed to make altered pressure wound therapy more comfortable with improved performance.

A best mode of the invention involves the utility of porous internal intermediates to wick away any excess wound fluids.

A second best mode of the invention involves the utility of less-porous intermediates when directing exudate flow to the outside margins of, and/or preventing semi-solid migration into, the intermediate material layer so specified is preferable.

A third best mode of the invention involves the utility of a hydrophobic foam, woven fabric or nonwoven including fibrotics and meshes as the top layer in a layered intermediate material to maximize moisture vapor transfer rates or gas permeation.

A fourth best mode of the invention employs biodegradable materials including proteinaceous matrix materials and lipids which augment wound healing.

One method of the invention may be operated by utilizing a porous matrix for at least one internal or top ply to drive capillary action toward the PAM. Another method of the invention may be operated by utilize non-porous materials to drive higher exudate velocities at the wound interface. Another method of the invention may be operated by utilizing a hydrophobic foam, woven fabric or nonwoven including fibrotics and meshes as the top layer in a layered intermediate material to maximize moisture vapor transfer rates or gas permeation.

The embodiments are further described by the following aspects:

1. The intermediate material layers disclosed herein selected optionally from the group of perforated and non perforated non-porous materials including silicone derivatives, latex rubber, polytetrafluoro-ethylene (PTFE), silicone elastomers, polymer hydromers, synthetic polymers, hydrocolloids, closed-cell foams, proteinaceous foams, lipogels, porous materials sealed by a sealant including semisolids, or any combination thereof.
2. The intermediate material layers disclosed herein selected optionally from the group of porous materials including woven materials, non-woven materials, open-cell foam, a synthetic sponge, a natural sponge, a fibrotic compact, a fibrotic nest, a proteinaceous foam, or any combination thereof.
3. The intermediate material layers disclosed herein where the layer is porous and composed individual openings averaging about 0.015 to 100 mm$^2$.
4. The intermediate material layers disclosed herein where the layer is porous and composed individual openings averaging about 0.062 to 25 mm$^2$.
5. The intermediate material layers disclosed herein where the layer is porous and composed individual openings averaging about 0.25 to 16 mm$^2$.

III. Designs to Maximize Percolation and Transference

Broadly a preferred system is disclosed in order to maximize the efficiency of exudate percolation and transference to the canister under negative altered pressures.

The system comprises an altered pressure apparatus comprising a covering means with a high moisture vapor transfer rate, thereby providing more gas penetration per unit time under negative altered pressures to hasten exudate percolation and transference to the canister.

The best mode of the invention employs a covering means adapted to provide a moisture vapor transfer rate in contact with water>10,000 g/m$^2$/24 hr measured at 37° C. and 10-90% relative humidity.

A second best mode of the invention employs a covering means adapted to provide a moisture vapor transfer rate in contact with water>7,500 g/m$^2$/24 hr measured at 37° C. and 10-90% relative humidity.

A third best mode of the invention employs a covering means adapted to provide a moisture vapor transfer rate in contact with water>3,750 g/m$^2$/24 hr measured at 37° C. and 10-90% relative humidity.

A fourth best mode of the invention employs a covering means adapted to provide a moisture vapor transfer rate in contact with water>3,750 g/m$^2$/24 hr used in combination with the semi-solids disclosed herein as a primary material.

One method of the invention may be operated by applying a covering means over a wound comprising a composition adapted to provide a moisture vapor transfer rate in contact with water>10,000 g/m$^2$/24 hr measured at 37° C. and 10-90% relative humidity; providing an opening in the covering means for a PAM to access or otherwise communicate with the Encapsulated space; and attaching the PAM to a canister in communication with an altered pressure source. Another method of the invention may be operated by applying a covering means over a wound comprising a composition adapted to provide a moisture vapor transfer rat e in contact with water>7,500 g/m$^2$/24 hr measured at 37° C. and 10-90% relative humidity; providing an opening in the covering means for a PAM to access or otherwise communicate with the Encapsulated space; and attaching the PAM to a canister in communication with an altered pressure source. Another method of the invention may be operated by applying a covering means over a wound comprising a composition adapted to provide a moisture vapor transfer rate in contact with water>3,750 g/m$^2$/24 hr measured at 37° C. and 10-90% relative humidity; providing an opening in the covering means for a PAM to access or otherwise communicate with the Encapsulated space; and attaching the PAM to a canister in communication with an altered pressure source. Another method of the invention may be operated by disposing a semi-solid as disclosed herein substantially at the tissue interface, optionally incorporating an intermediate material; applying a covering means over a wound comprising a composition adapted to provide a moisture vapor transfer rate in contact with water>3,750 g/m$^2$/24 hr measured at 37° C. and 10-90% relative humidity; providing an opening in the covering means for a PAM to access or otherwise communicate with the Encapsulated space; and attaching the PAM to a canister in communication with an altered pressure source.

The embodiments are further described by the following aspects:
1. An altered pressure apparatus comprising a covering means where the moisture vapor transfer rate in contact with water is >1,000 g/m$^2$/24 hr measured at 37° C. and 10-90% relative humidity.
2. The altered pressure apparatus of item 1 where the moisture vapor transfer rate in contact with water is >4,000 g/m$^2$/24 hr measured at 37° C. and 10-90% relative humidity.
3. The altered pressure apparatus of item 1 where the moisture vapor transfer rate in contact with water is >7,000 g/m$^2$/24 hr measured at 37° C. and 10-90% relative humidity.
4. The altered pressure apparatus of item 1 where the moisture vapor transfer rate in contact with water is >10,000 g/m$^2$/24 hr measured at 37° C. and 10-90% relative humidity.
5. The altered pressure apparatus of item 1 where the moisture vapor transfer rate in contact with water is >13,000 g/m$^2$/24 hr measured at 37° C. and 10-90% relative humidity.
6. The altered pressure apparatus of item 1 where the moisture vapor transfer rate in contact with water is >16,000 g/m$^2$/24 hr measured at 37° C. and 10-90% relative humidity.
7. The altered pressure apparatus of item 1 where the moisture vapor transfer rate in contact with water is >19,000 g/m$^2$/24 hr measured at 37° C. and 10-90% relative humidity.
8. The altered pressure apparatus of item 1-7 further comprising a semi-solid material within the encapsulated space as described herein.
9. The altered pressure apparatus of item 1-8 where the negative altered pressures for treatment are less than 105 mm Hg.

Broadly a preferred system is disclosed to maximize the efficiency of exudate percolation and transference to the canister under negative altered pressures and to provide for easier removal of the dressing including less pain for the patient subsequent to altered pressure therapy.

The system comprises an altered pressure apparatus comprising a covering means adapted to include a sealing means with at least one zone of adhesive void, or substantially reduced zone, thereby providing a high moisture vapor transfer rate and easier removal force.

Figure 5:
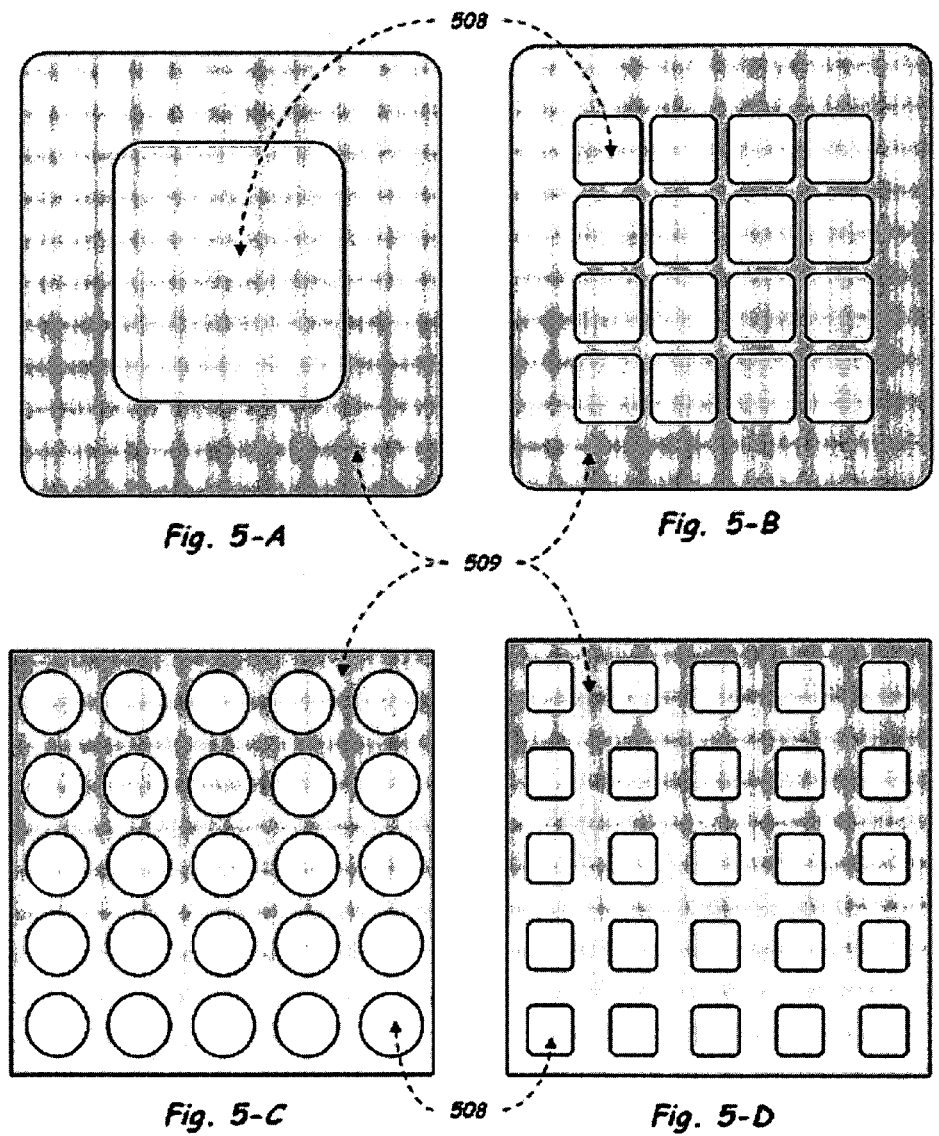
FIG. 5 shows a bottom view of Covers comprising zones of adhesive voids.

Referring to FIG. 5, the best mode of the invention employs a covering means adapted to include a sealing means with a zone of adhesive void.

Referring to FIG. 5, a second best mode of the invention employs a covering means adapted to include a sealing means with multiple zones of adhesive void.

A third best mode of the invention employs a sealing means comprising an acrylic or silicone based composition.

A fourth best mode of the invention employs a covering means adapted to include a sealing means with at least one zone of adhesive void with a moisture vapor transfer rate in contact with water>7,500 g/m$^2$/24 hr measured at 37° C. and 10-90% relative humidity.

A fifth best mode of the invention employs a covering means adapted to include a sealing means with at least one zone of adhesive void with a moisture vapor transfer rate in contact with water>3,750 g/m²/24 hr measured at 37° C. and 10-90% relative humidity.

A Sixth best mode of the invention employs covering means adapted to include a sealing means with at least one zone of adhesive void used in combination with the semi-solids disclosed herein as a primary material.

One method of the invention may be operated by applying a covering means adapted to include a sealing means with a single central zone of adhesive void over a wound; providing an opening in the covering means for a PAM to access or otherwise communicate with the Encapsulated space; and attaching the PAM to a canister in communication with an altered pressure source. Another method of the invention may be operated by applying a covering means adapted to include a sealing means with multiple zones of adhesive void over a wound; providing an opening in the covering means for a PAM to access or otherwise communicate with the Encapsulated space; and attaching the PAM to a canister in communication with an altered pressure source. Another method of the invention may be operated by applying a covering means adapted to include a sealing means with at least one zone of adhesive void over a wound, said covering means comprising a composition adapted to provide a moisture vapor transfer rate in contact with water>3,750 g/m²/24 hr measured at 37° C. and 10-90% relative humidity; providing an opening in the covering means for a PAM to access or otherwise communicate with the Encapsulated space; and attaching the PAM to a canister in communication with an altered pressure source. Another method of the invention may be operated by disposing a semi-solid as disclosed herein substantially at the tissue interface, optionally incorporating an intermediate material including layered intermediate materials; applying a covering means adapted to include a sealing means with at least one zone of adhesive void over a wound; providing an opening in the covering means for a PAM to access or otherwise communicate with the Encapsulated space; and attaching the PAM to a canister in communication with an altered pressure source.

The embodiments are further described by the following aspects:

1. An altered pressure apparatus comprising a covering means adhesively coated to provide a sealing means as a part of thereof; said adhesive coating further comprising at least one zone of void where the adhesive is missing or substantially reduced in comparison to the adhesive quantity around the zone of void.
2. The altered pressure apparatus of item 1 where the adhesive coating comprises one central zone void.
3. The altered pressure apparatus of item 1 where the adhesive coating comprises multiple zone voids.
4. The altered pressure apparatus of items 1-3 where the adhesive coating is non-latex based.
5. The altered pressure apparatus of item 4 where the adhesive coating includes a silicone based composition, an acrylic based composition or any combination thereof.
6. The altered pressure apparatus of item 1-5 where the covering means provides a moisture to vapor transfer rate in contact with water>1,000 g/m²/24 hr measured at 37° C. and 10-90% relative humidity.
7. The altered pressure apparatus of item 1-5 where the covering means comprises a composition that is at least partially hydrophilic.
8. The altered pressure apparatus of item 6-7 where the composition is at least partially comprised of polyurethane.
9. The altered pressure apparatus of item 6-7 where the composition when hydrated absorbs 10-60% water.
10. The altered pressure apparatus of item 1-9 where the total zones of void are >10% of the surface area disposed over the wound area.
11. The altered pressure apparatus of item 1-10 further comprising a semi-solid material within the encapsulated space as described herein.
12. The altered pressure apparatus of item 1-11 where the negative altered pressures for treatment are less than 105 mm Hg.

IV. Pressure Monitoring & Control System with Integrated Disposable Filter

Broadly a preferred system is disclosed to measure the pressure within the encapsulated space to at least a clinically relevant certainty, provide a feedback signal to a control means, and to provide a filtering means to the canister effluent which, in combination, provides the clinician accurate measurements, precise control, greater convenience, less cross contamination, improved compliance and the patient less pain and trauma.

The system comprises a means for monitoring the pressure between the wound and the canister outlet, the apparatus further comprising a filter contained within the canister adapted to filter the canister effluent.

Figure 6:
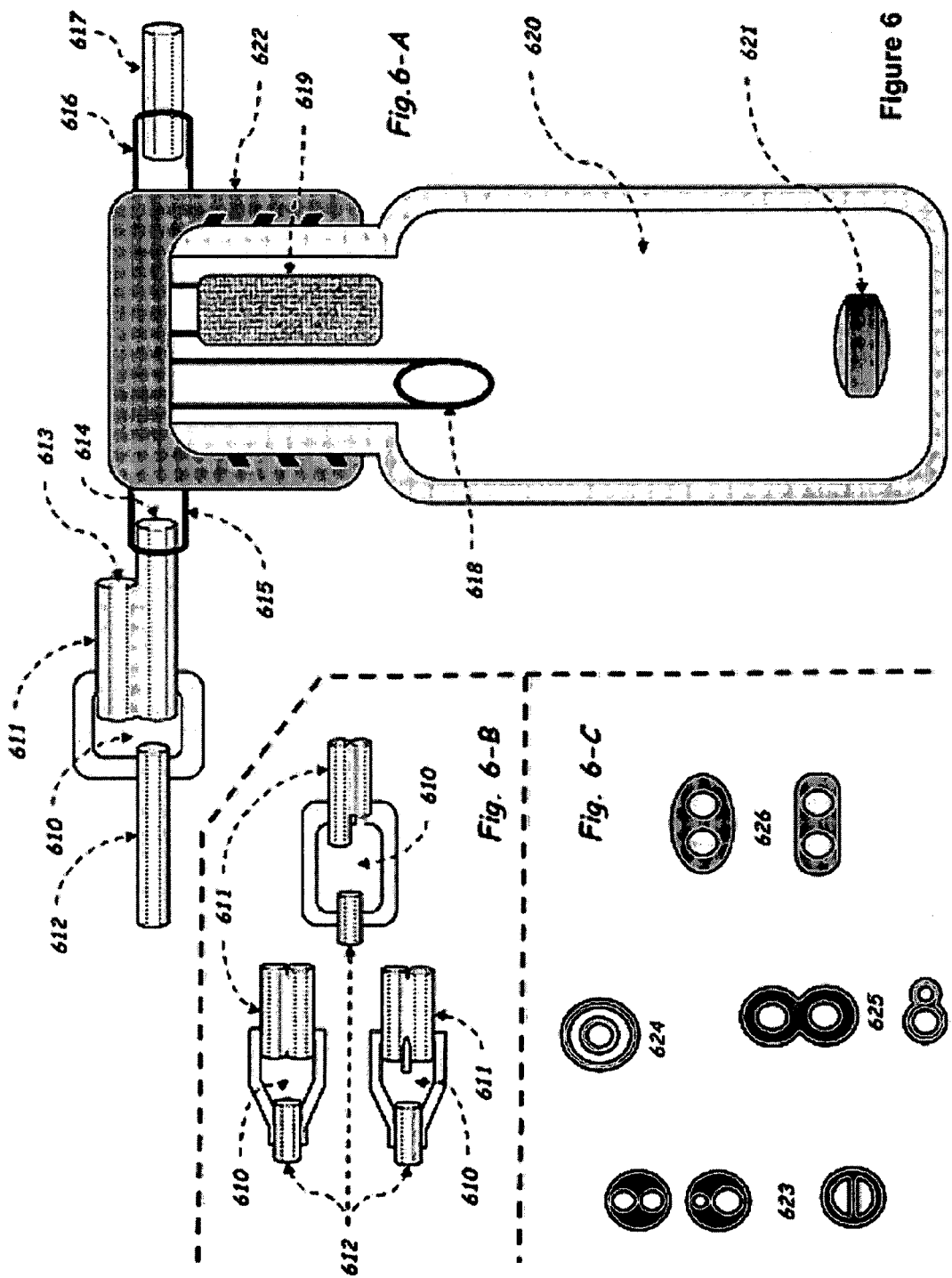
FIG. 6 shows a partially dissected view of a multi-lumen feedback & filtering system. The system is illustrated with a simple removable top canister design.
Figure 7:
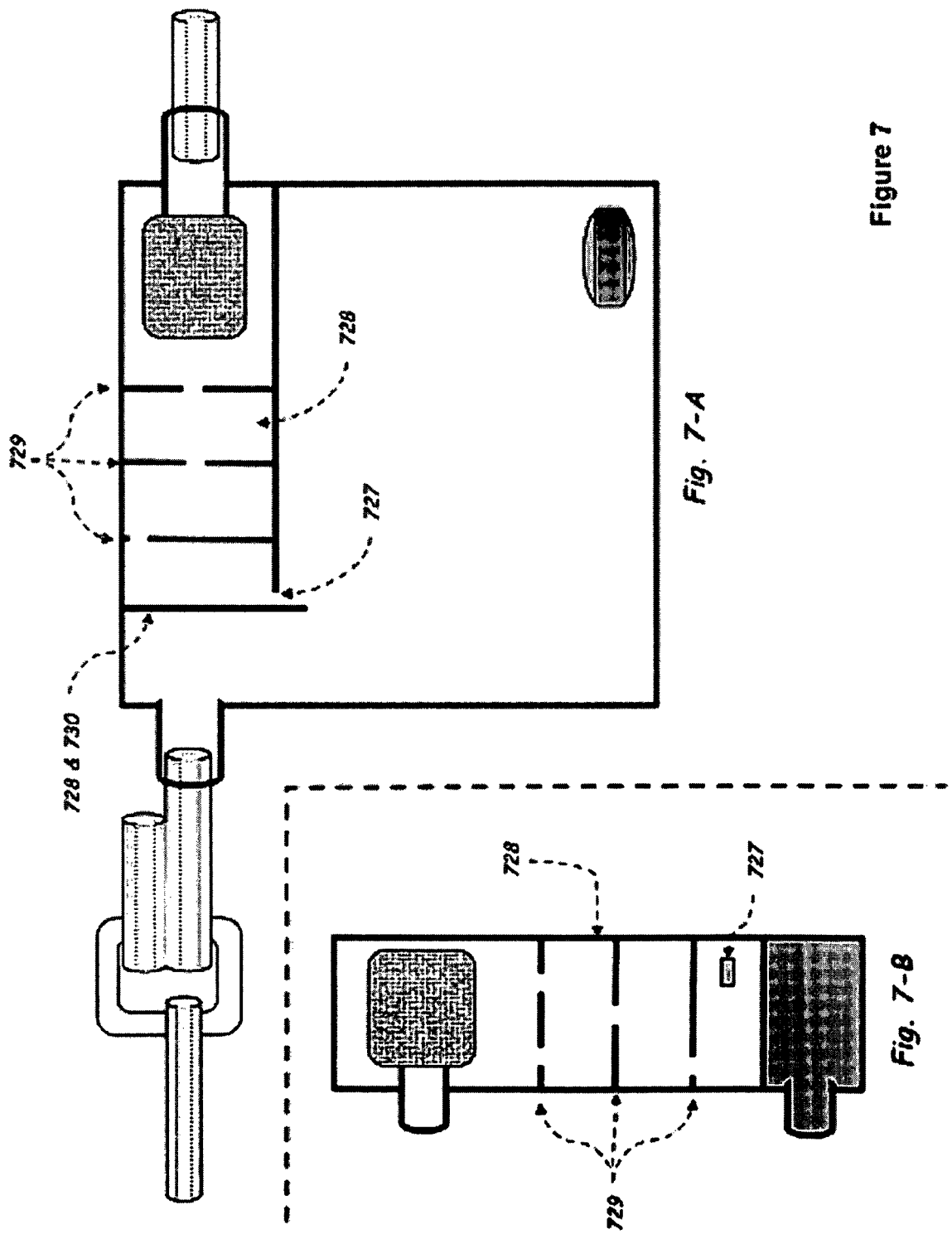
FIG. 7 shows a partially dissected view of a multilumen feedback & filtering system. The system is illustrated with a first fixed top canister design.

Referring to FIGS. 6-8, the best mode of the invention employs a means for monitoring the pressure inside or outside of the encapsulated space within 10 cm from any PAM access opening in the cover, the apparatus further comprising a filter contained within the canister adapted to filter canister effluent.

Referring to FIGS. 6-8, a second best mode of the invention employs a means for monitoring the pressure located outside of the encapsulated space 10-120 cm from any PAM access opening in the cover, the apparatus further comprising a filter contained within the canister adapted to filter canister effluent.

Referring to FIGS. 6-8, a third best mode of the invention employs a means for monitoring the pressure located outside of the encapsulated space>120 cm from any PAM access opening in the cover up to the canister inlet, the apparatus further comprising a filter contained within the canister adapted to filter canister effluent.

A fourth best mode of the invention employs a means for monitoring the pressure located outside of the encapsulated space via the space within the canister, the apparatus further comprising a filter contained within the canister adapted to filter canister effluent.

Referring to FIGS. 7 & 8, a fifth best mode of the invention employs a protective partial enclosure for the filter contained within the canister adapted to filter canister effluent, thereby inhibiting blinding by canister fluids.

One method of the invention may be operated by acquiring a pressure communication from the terminal proximal end of the PAM via at least one lumen independent of any lumen delivering an altered pressure to the encapsulated space, said communication connected to a detector; providing a signal input from said detector to a controlling means; providing a canister comprising a filter contained within to filter the effluent at the outlet, said canister disposed between the wound and pressure source of any negative altered pressure lumen; and utilizing said controlling means to regulate an altered pressure source, thereby controlling the pressure in the encapsulated space. Another method of the invention may be operated by acquiring a pressure communication from a partially capsulated union disposed between the terminal end of the PAM and the canister inlet via at least one lumen independent of any lumen delivering an altered pressure to the encapsulated space, said communication connected to a detector; providing a signal input from said detector to a controlling means; providing a canister comprising a filter contained within to filter the effluent at the outlet, said canister disposed between the wound and pressure source of any negative altered pressure lumen; and utilizing said controlling means to regulate an altered pressure source, thereby controlling the pressure in the encapsulated space. Another method of the invention may be operated by acquiring a pressure communication from a canister via at least one lumen independent of any lumen delivering an altered pressure to the encapsulated space, said communication connected to a detector, said canister comprising a filter contained within to filter the effluent at the outlet, said canister disposed between the wound and pressure source of any negative altered pressure lumen; providing a signal input from said detector to a controlling means; and utilizing said controlling means to regulate an altered pressure source, thereby controlling the pressure in the encapsulated space.

The embodiments are further described by the following aspects:

1. An altered pressure apparatus where the PAM is comprised of a means for monitoring the pressure inside or outside of the encapsulated space within 10 cm from any PAM access opening in the cover, thereby providing input for a controlling means to regulate the pressure drive provided by the pressure source within a specified value and tolerance.
2. The PAM of item 1 at least partially further comprised of one tube, or one conduit, composed of at least dual lumen (two independent lumen) where: (a) one lumen delivers the altered pressure directly or indirectly from the pressure source to the proximal end, and (b) the other lumen provides feedback from the proximal end to the controlling means.
3. The PAM of item 1 at least partially further comprised two side by side tubes, or conduits, each containing an independent lumen (aka one lumen per tube/conduit), at least partially attached by one or several lateral connections where: (a) one lumen delivers the altered pressure directly or indirectly from the pressure source to the proximal end, and (b) the other lumen provides feedback from the proximal end to the controlling means.
4. The PAM of item 3 where the connection is continuous for the length of the tubes or conduits.
5. The PAM of item 3 where the connection is intermittent for the length of the tubes or conduits.
6. The PAM of item 3 where the connection is intermittent and removable.
7. The PAM of item 1 at least partially further comprised of a coaxial conduit where (a) the inner most lumen of the coax delivers the altered pressure directly or indirectly from the pressure source to the proximal end, and (b) the outer most lumen of the coax provides feedback from the proximal end to the controlling means.
8. An altered pressure apparatus where the PAM is comprised of a means for monitoring the pressure located outside of the encapsulated space 10-120 cm from any PAM access opening in the cover, or >120 cm from any PAM access opening in the cover up to the canister inlet, thereby providing input for a controlling means to regulate the pressure drive provided by the pressure source within a specified value and tolerance.
9. The PAM of item 8 at least partially further comprised of one tube, or one conduit, composed of dual lumen (two independent lumen) where: (a) one lumen delivers the altered pressure directly or indirectly from the pressure source to the proximal end, and (b) the other lumen provides feedback from the proximal end to the controlling means.
10. The PAM of item 8 at least partially further comprised two side by side tubes, or conduits, each containing an independent lumen (aka one lumen per tube/conduit), at least partially attached by one or several lateral connections where: (a) one lumen delivers the altered pressure directly or indirectly from the pressure source to the proximal end, and (b) the other lumen provides feedback from the proximal end to the controlling means.
11. The PAM of item 10 where the connection is continuous for the length of the tubes or conduits.
12. The PAM of item 10 where the connection is intermittent for the length of the tubes or conduits.
13. The PAM of item 10 where the connection is intermittent and removable.
14. The PAM of item 8 at least partially further comprised of a coaxial conduit where (a) the inner most lumen of the coax delivers the altered pressure directly or indirectly from the pressure source to the proximal end, and (b) the outer most lumen of the coax provides feedback from the proximal end to the controlling means.
15. The PAM of items 1-14 wherein the means for monitoring the pressure includes a partially capsulated union, located outside of the encapsulated space, and adapted to provide a pressure feedback sensing space to the PAM by connecting a multiple passage means, including a dual lumen design, a two side by side tube design or a coaxial conduit design, to the partially capsulated union.
16. The PAM of item 15 wherein the terminating section of the PAM, which communicates the encapsulated space to the partially capsulated union, is constructed of a passage, tubing or conduit with only one connecting opening to the encapsulated space.
17. The PAM of item 15-16 wherein the capsulated union is also a bulk collection means.
18. The PAM of item 15-16 wherein the capsulated union is independent of the bulk collection means.
19. The PAM of items 1-7 and 8-18 further comprising a pressure sensing means located at the proximal or medial section of the PAM; where the pressure value detected is transferred by a transmitter of electromagnetic radiation, including radio waves, to a receiver communicating with a controlling means; thereby providing input for a controlling means to regulate the pressure drive provided by the pressure source within a specified value and tolerance.
20. The altered pressure apparatus of items 1-19 further comprising at least one filter located inside the canister, adapted to filter the outlet effluent, and disposed substantially at the opening of the outlet of said canister.
21. The altered pressure apparatus of item 20 where the filter or filters are adapted to retard the passage of wound exudate, odor or bacteria including a hydrophobic composition, a charcoal composition, a composition with a porosity of <0.3 micron, or any combination thereof as non-limiting examples.
22. The altered pressure apparatus of item 21 where the filter or filters are at least partially protected from blinding from canister fluids by a partial wall of separation from the inlet.
23. The altered pressure apparatus of item 21 where the filter or filters are at least partially protected from blinding from canister fluids by partial enclosure.
24. The altered pressure apparatus of item 23 where the partial enclosure comprises at least one baffle partition.
25. The altered pressure apparatus of item 23 where the partial enclosure comprises at least one secondary filter independent of the primary filter; said primary filter adapted to retard the passage of wound exudate, odor or bacteria.

26. The altered pressure apparatus of items 20-25 comprising an alarm to denote at least the partial blinding of any of said filters by canister fluids.
27. The altered pressure apparatus of item 26 where a detector including pressure and flow rate detectors provide the signal to discharge the alarm.
28. The altered pressure apparatus of item 1-27 further comprising a semi-solid material within the encapsulated space as described herein.
29. The altered pressure apparatus of item 1-28 where the negative altered pressures for treatment are less than 105 mm Hg.

V. Ancillary Aspects

Broadly ancillary aspects and embodiments are disclosed which improve the performance of altered pressure wound therapy, make the treatments more comfortable for the patient and the delivery of the treatment more convenient for clinicians.

Many variations of the invention will occur to those skilled in the art. Some variations include:
The embodiments described by the following aspects:

1. The apparatus disclosed herein where the components of the dressing, PAM or the bulk collection means including containers, closures, liners, spill catches and shrouds, intermediate materials, secondary materials, covering means, sealing means, cushioning means and any combination thereof are sold in Kits.
2. The PAM disclosed herein consisting of a splitting means between the medial section and proximal end, adapted to add additional medial and proximal sections for the treatment of more than one wound.
3. The altered pressure apparatus disclosed herein where the altered pressure source is comprised of a means to program regimens or batches for automated control of treatment cycles.
4. The PAM disclosed herein having a means of disconnection and replacement of the proximal section and optionally medial section of the PAM.
5. The altered pressure apparatus disclosed herein further comprising injection or infusion port with a sealing means for the delivery of liquids to the encapsulated space, located upon the covering or PAM.
6. An altered pressure apparatus where the PAM is comprised of at least one means to control flow in one direction.

All such variations are intended to be within the scope and spirit of the invention.

Although some embodiments are shown to include certain features, the applicant(s) specifically contemplate that any feature disclosed herein may be used together or in combination with any other feature on any embodiment of the invention. It is also contemplated that any feature may be specifically excluded from any embodiment of an invention.

EXAMPLES

|  | Top Layer | Middle Layer | Bottom Layer |
|---|---|---|---|
| Example 1 | PU Foam-20 PPI-10 mm | None | PU Foam-100 PPI-20 mm |
| Example 2 | PU Foam-100 PPI-25 mm | None | PU Foam-20 PPI-5 mm |
| Example 3 | PU Foam-15 PPI-10 mm | None | PU Foam-30 PPI-20 mm |
| Example 4 | PU Foam-20 PPI-10 mm | PU Foam-50 PPI-15 mm | PU Foam-100 PPI-5 mm |
| Example 5 | PU Foam-100 PPI-5 mm | PU Foam-50 PPI-20 mm | PU Foam-20 PPI-5 mm |
| Example 6 | PU Foam-30 PPI-5 mm | PU Foam-80 PPI-20 mm | PU Foam-30 PPI-5 mm |
| Example 7 | PU Foam-15 PPI-5 mm | PU Foam-80 PPI-15 mm | PU Foam-20 PPI-10 mm |

PPI = pores per inch/PU = polyurethane

The above described polyurethane foams were laminated with acrylic adhesive, other than one example laminated by heat. The resulting intermediate materials provided a bottom morphology appropriate for a tissue interface or a hydrophobic semi-solid primary material interface with high comfort properties while maintaining adequate exudate flow rates and uniform flow patterns under negative pressures. Under negative pressure, these examples controlled the migration of the said semisolid while providing excellent exudate drainage. The foams may be hydrophobic or hydrophilic but the top layers were preferred to be hydrophobic or off large pore size.

|  | Top Layer | Middle Layer | Bottom Layer |
|---|---|---|---|
| Example 8 | Polyester Textile | None | PU Foam-100 PPI-30 mm |
| Example 9 | Polyester Textile | None | PU Foam-20 PPI-30 mm |
| Example 10 | Polyester Textile | None | PU Foam-30 PPI-30 mm |
| Example 11 | Nylon Mesh | None | PU Foam-100 PPI-30 mm |
| Example 12 | Nylon Mesh | None | PU Foam-20 PPI-30 mm |
| Example 13 | Nylon Mesh | None | PU Foam-30 PPI-30 mm |
| Example 14 | PU Foam-100 PPI-30 mm | None | Nylon Mesh |
| Example 15 | PU Foam-20 PPI-30 mm | None | Calcium Alginate Fibrotic |

-continued

|  | Top Layer | Middle Layer | Bottom Layer |
|---|---|---|---|
| Example 16 | PU Foam-30 PPI-30 mm | None | Polyester Textile |
| Example 17 | Polyester Textile | PU Foam-20 PPI-30 mm | Polyester Textile |
| Example 18 | Rayon Textile | PU Foam-20 PPI-30 mm | Nylon Mesh |
| Example 19 | Nylon Mesh | PU Foam-20 PPI-30 mm | Calcium Alginate Fibrotic |
| Example 20 | Nylon Mesh | PU Foam-20 PPI-30 mm | Nylon Mesh |
| Example 21 | Polyurethane Mesh | PU Foam-80 PPI-20 mm | PU Foam-20 PPI-10 mm |
| Example 22 | Calcium Alginate Fibrotic | PU Foam-30 PPI-30 mm | Calcium Alginate Fibrotic |
| Example 23 | PU Foam-30 PPI-20 mm | Polyester Textile | PU Foam-30 PPI-10 mm |

PPI = pores per inch/PU = polyurethane

The layers described above were laminated with acrylic adhesive, other than one example laminated by heat. The resulting intermediate materials provided a bottom morphology appropriate for a tissue interface or a hydrophobic semi-solid primary material interface with high comfort properties while maintaining adequate exudate flow rates and uniform flow patterns under negative pressures. Under negative pressure, these examples controlled the migration of the said semisolid while providing excellent exudate drainage. The foams may be hydrophobic or hydrophilic.

| Example 24 | Purified Water, USP | 7% |
|---|---|---|
|  | Glyceryl monooleate | 93% |
| Example 25 | Ethanol, USP | 1.5% |
|  | Purified Water, USP | 8.5% |
|  | Glyceryl monooleate | 90% |
| Example 26 | Ethanol, USP | 1.5% |
|  | Purified Water, USP | 8.5% |
|  | Capric Acid | 0.22% |
|  | Lauric Acid | 0.25% |
|  | Glyceryl monooleate | 89.53% |
| Example 27 | Ethanol, USP | 1.5% |
|  | Purified Water, USP | 10.5% |
|  | Capric Acid | 2% |
|  | Lauric Acid | 2% |
|  | Monoerucin | 84% |
| Example 28 | Ethanol, USP | 3.5% |
|  | Purified Water, USP | 3.5% |
|  | Silver Acetate | 1% |
|  | Glyceryl monooleate | 92% |

The resulting mixtures produced gel formulations with relatively low viscosities. The gels had very limited migration during testing and thus are deemed well suited as hydrophobic semisolids for use with altered pressure therapy. The above compositions were also tested for the ability to inhibit biofilm formation in a multispecies in vitro model. Concentrations as low as 0.1% were able to prevent biofilm formation. Concentrations as low as 0.005% still had significant activity against biofilms.

The present examples 1-28 possess characteristics making them operable intermediate materials for altered pressure therapy. The constructs above may be applied to any acute or chronic wound directly prior to application of the altered pressure. These examples were evaluated by the inventors with altered pressure apparatuses as described herein. The constructs are particularly adapted to filling even small void spaces, directing fluid flow, providing a cushioning effect, delivering active agents for durations exceeding dressing change schedules, preventing tissue in growth into foreign materials and providing an anti-adherence function to the dressings. The examples containing antimicrobials or biofilm agents are provided as non-limiting examples of the inventions ability to provide sustained release of actives which augment wound healing.

We claim:

1. An altered pressure device for treating a wound in an encapsulated space delimited by a cover secured over a wound, the device comprising: (a) an altered pressure source communicating with the encapsulated space via a length of tubing coupled with the source; and (b) layered intermediate materials composed of at least one foam layer laminated to at least one additional layer, wherein a top layer of the layered intermediate materials, which is one of the at least one foam layer and the at least one additional layer, comprises structural characteristics that enable gas permeation into the encapsulated space when interfacing with the cover, and wherein at least a bottom layer of the layered intermediate materials, which is another of the at least one foam layer and the at least one additional layer, is constructed to discourage tissue in growth and provide an anti-adherence function, the bottom layer being a tissue contact layer,
wherein at least one layer of the layered intermediate materials is a hydrophobic semi-solid wound dressing interfacing with wound tissue and adhering to at least one of the layered intermediate materials.

2. A device according to claim 1, wherein the at least one additional layer is a woven material.

3. A device according to claim 1, wherein the at least one additional layer is a nonwoven material.

4. A device according to claim 1, wherein the at least one foam layer is comprised of one of perforated and non perforated closed-cell foam including a proteinaceous foam, a polyurethane foam and a polyvinyl alcohol foam.

5. A device according to claim 1, wherein the at least one foam layer is comprised of a porous open-cell foam including a proteinaceous foam, a polyurethane foam and a polyvinyl alcohol foam.

6. A device according to claim 1, wherein the at least one additional layer is comprised of one of perforated and non perforated non-porous material including a silicone derivative, a latex rubber, a polytetrafluoro-ethylene (PTFE), a silicone elastomer, a polymer hydromer, a synthetic polymer, a hydrocolloid, or any combination thereof.

7. A device according to claim 1, wherein the at least one additional layer is comprised of a porous material including one of woven materials, non-woven materials, a fibrotic compact, a fibrotic nest, or any combination thereof.

8. A device according to claim 1, wherein the cover comprises structural characteristics that provide a moisture vapor transfer rate greater than 2,000 g/m2/24 hr.

9. A device according to claim 1, wherein the cover comprises at least one zone of void where adhesive is missing or substantially reduced.

10. A device according to claim 1, further comprising a negative pressure greater than 0 mm Hg but less than 105 mm Hg relative to atmospheric.

11. A device according to claim 1, further comprising means for controlling multiple altered pressure cycles in sequence, each pressure cycle composed of a specified target non-atmospheric value for a specified target duration.

12. A device according to claim 11, further comprising at least one negative pressure cycle greater than 0 mm Hg but less than 60 mm Hg relative to atmospheric.

13. A device according to claim 1, wherein the top layer of the layered intermediate materials is the at least one additional layer.

\* \* \* \* \*